Figure 1:
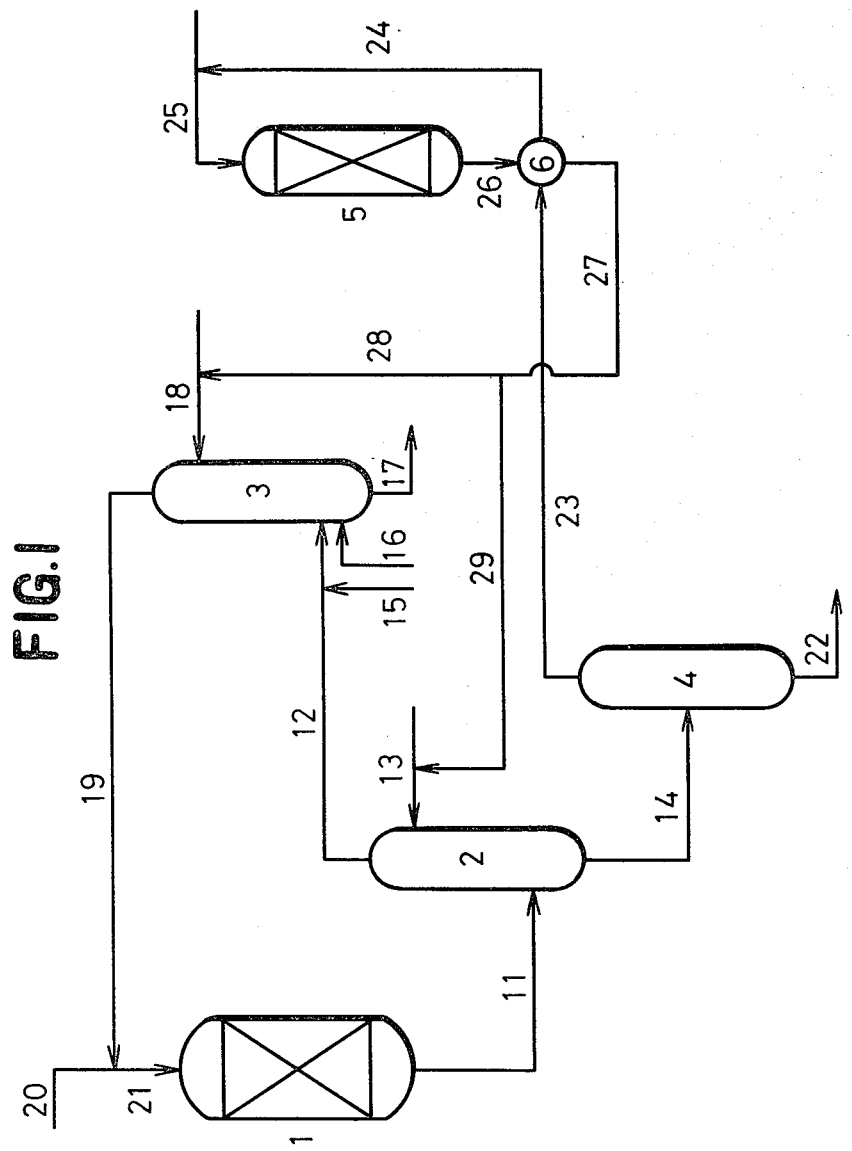

United States Patent [19]

Tahara et al.

[11] Patent Number: 4,467,109
[45] Date of Patent: Aug. 21, 1984

[54] PROCESS FOR CONTINUOUS PREPARATION OF DIESTER OF OXALIC ACID

[75] Inventors: Susumu Tahara; Kozo Fujii; Keigo Nishihira; Masaoki Matsuda; Katsuhiko Mizutare, all of Ube, Japan

[73] Assignee: Ube Industries, Ltd., Ube, Japan

[21] Appl. No.: 495,460

[22] Filed: May 19, 1983

Related U.S. Application Data

[63] Continuation of Ser. No. 293,702, Aug. 17, 1981, abandoned.

[30] Foreign Application Priority Data

Aug. 29, 1980 [JP] Japan .................................. 118343

[51] Int. Cl.$^3$ ............................................ C07C 69/34
[52] U.S. Cl. .................................. 560/193; 560/190; 560/204
[58] Field of Search ..................... 560/204, 190, 193

[56] References Cited

U.S. PATENT DOCUMENTS 4,229,589 10/1980 Nishimura et al. ................. 560/204
4,229,591 10/1980 Nishimura et al. ................. 560/204

FOREIGN PATENT DOCUMENTS 2025950 1/1980 United Kingdom ............... 560/204

*Primary Examiner*—Alan Siegel
*Attorney, Agent, or Firm*—Frishauf, Holtz, Goodman & Woodward

[57] ABSTRACT

There is provided a process for the continuous preparation of a diester of oxalic acid, which comprises a first step of reacting carbon monoxide with an ester of nitrous acid in the gaseous phase; a second step of condensing the gaseous reaction mixture to separate a non-condensed gas from a condensed liquid containing the diester of oxalic acid; a third step of introducing the non-condensed gas of the second step to a regeneration column, thereby contacting it with a gas containing molecular oxygen and an alcohol, and recycling the resulting gas containing an ester of nitrous acid to the reactor of the first step; a fourth step of distilling out an alcohol containing a diester of carbonic acid formed as a by-product of the first step and obtaining a liquid diester of oxalic acid; and a fifth step of introducing the distillate of the fourth step to a hydrolysis column thereby hydrolyzing the diester of carbonic acid in the gas and recycling the alcohol as an alcohol source for the third step.

18 Claims, 1 Drawing Figure

PROCESS FOR CONTINUOUS PREPARATION OF DIESTER OF OXALIC ACID

This is a continuation of application Ser. No. 293,702, filed Aug. 17, 1981, now abandoned.

The present invention relates to a novel process for preparing a diester of oxalic acid, and particularly to a novel process whereby the production of a diester of oxalic acid is industrially advantageously carried out by a gaseous phase reaction with use of carbon monoxide and an ester of nitrous acid as the starting materials in the presence of a solid catalyst of platinum group metal series.

Diesters of oxalic acid have been used as important starting materials for the syntheses of oxalic acid, oxamide, glycols, intermediates for dyes and pharmaceuticals.

There has hitherto been known a process for preparing a diester of oxalic acid by contacting carbon monoxide and an ester of nitrous acid with a solid catalyst of platinum group metal series in the gaseous phase. This reaction itself is an extremely good reaction for the preparation of diesters of oxalic acid. However, in order to employ this reaction industrially, it is necessary to have a process whereby the reaction can be conducted continuously as is the case for other chemical reactions.

The present inventors have conducted extensive researches with an aim to establish an industrially advantageous continuous process for the production of diesters of oxalic acid by contacting carbon monoxide and an ester of nitrous acid with a solid catalyst of platinum group metal series in the gaseous phase. As a result, it has been found that it is possible to obtain diesters of oxalic acid industrially extremely advantageously by employing a process which comprises;

(1) a first step of introducing a gas containing carbon monoxide and an ester of nitrous acid into a reactor packed with a solid catalyst carrying a platinum group metal or its salt, and thereby conducting a catalytic reaction in the gaseous phase to obtain a product containing a diester of oxalic acid;

(2) a second step of introducing the product of the first step to a condenser thereby to separate a non-condensed gas containing nitrogen monoxide formed by the catalytic reaction of the first step from a condensed liquid containing the diester of oxalic acid;

(3) a third step of introducing the non-condensed gas of the second step to a regeneration column, thereby contacting it with a gas containing molecular oxygen and an alcohol, and recycling the resulting gas containing an ester of nitrous acid to the reactor of the first step;

(4) a fourth step of introducing the condensed liquid of the second step to a distillation column and thereby distilling out an alcohol containing a diester of carbonic acid formed as a by-product by the catalytic reaction of the first step, and obtaining a liquid diester of oxalic acid; and (5) a fifth step of introducing the distillate of the fourth step to a hydrolysis column thereby hydrolyzing the diester of carbonic acid in the gas and recycling the alcohol thereby obtained, as an alcohol source for the third step.

Now, each step of the present invention will be described.

FIRST STEP

A gaseous starting material containing carbon monoxide and an ester of nitrous acid, is introduced into a reactor packed with a solid catalyst of platinum group metal series, and thereby a catalytic reaction is carried out in the gaseous phase.

As the reactor, a single tubular or multi-tubular column packed with a catalyst is useful. The contact time of the gaseous starting material with the solid catalyst of platinum metal series is set to be at most 10 seconds, preferably from 0.2 to 5 seconds.

As the solid catalyst of platinum group metal series, palladium is most useful, but platinum, rhodium, ruthenium, and iridium are also useful. Further, salts of these metals such as nitrates, sulfates, phosphates, halides, acetates, oxalates or benzoates, may be used. These materials are used as carried by an inert carrier such as active carbon, alumina, silica, diatom earth, pumice, zeolite, or Molecular Sieve. The amount to be used, in terms of the platinum group metal, is within a range of from 0.01 to 10% by weight, usually from 0.2 to 2% by weight, relative to the carrier.

The gaseous starting material, i.e., a gas containing carbon monoxide and an ester of nitrous acid may usually be used in a form diluted with an inert gas such as nitrogen or carbon dioxide.

The ester of nitrous acid may preferably be an ester of a saturated monohydric aliphatic or alicyclic alcohol having from 1 to 8 carbon atoms with nitrous acid. As the alcohol component, there may be mentioned, for instance, an aliphatic alcohol such as methanol, ethanol, n- (and iso-)propanol, n- (iso-, sec- and tert-)butanol, n- (and iso-)amyl alcohol, hexanol, or octanol, and an alicyclic alcohol such as cyclohexanol, or methylcyclohexanol. These alcohols may contain a substituent, such as an alkoxy group, which does not hinder the reaction. Among these, methyl nitrite is most preferably used.

It is necessary to carry out this reaction under such conditions that there is no formation of a liquid phase in the reaction zone. The conditions for no formation of a liquid phase in the reaction zone vary depending upon the reaction temperature, the reaction pressure and the kind and concentration of the ester of nitrous acid used, and therefore can not simply be determined.

However, with respect to the reaction temperature, the reaction proceeds in a sufficiently high speed even at a low temperature, and the lower the reaction temperature is, the less side reactions occur. Accordingly, so long as the desired time yield can be maintained, the reaction is carried out at a relatively low temperature, i.e. usually from 50° to 200° C., preferably from 80° to 150° C. Further, with respect to the reaction pressure, the reaction is carried out usually under a pressure from ambient pressure to 10 kg/cm$^2$ (gauge pressure), preferably from ambient pressure to 5 kg/cm$^2$ (gauge pressure). However, in some cases, the reaction pressure may be slightly lower than ambient pressure.

The concentration of the ester of nitrous acid in the gaseous starting material may be varied over a wide range. However, in order to attain a satisfactory reaction rate, it is necessary to adjust the concentration to be at least 1% by volume, usually from 5 to 30% by volume.

The concentration of carbon monoxide in the gaseous starting material may be varied over a wide range, and is usually selected within a range of from 10 to 90% by volume.

SECOND STEP

The product of the first step is led to a condenser, cooled to a temperature at which the diester of oxalic acid in the product is condensed, and separated into a condensed liquid and a non-condensed gas.

The condensed liquid thus separated, contains small amounts of by-products such as a diester of carbonic acid, and an ester of formic acid, in addition to the intended diester of oxalic acid. On the other hand, the non-condensed gas contains non-reacted carbon monoxide, an ester of nitrous acid and the like, in addition to the nitrogen monoxide formed by the catalytic reaction of the first step.

Further, during this step, a part of the intended diester of oxalic acid is carried by the non-condensed gas, and then hydrolized by water formed during the regeneration of nitrogen monoxide in the subsequent third step, and it is possible that the resulting oxalic acid accumulates within the gas recycling system. Furthermore, when the intended product is the one having a relatively high melting point, such as dimethyl oxalate, it is possible that the intended product solidifies and deposits on the wall of the condenser and finally plugs off the condenser.

In order to solve these problems, it is possible to employ a method wherein the product of the first step is cooled for condensation at a temperature of at most the boiling point of an alcohol while contacting it with an alcohol, preferably an alcohol having 1 to 4 carbon atoms. For instance, when the intended product is dimethyl oxalate, it is preferred that the cooling and condensation are carried out at a temperature of from 30° to 60° C. while supplying from 0.01 to 0.1 part by volume of methanol, relative to 100 parts by volume of the product to be treated.

THIRD STEP

The non-condensed gas separated in the second step is led to a regeneration column and contacted with a gas containing molecular oxygen and an alcohol thereby to regenerate nitrogen monoxide in the gas into an ester of nitrous acid.

As the regeneration column for this step, a usual gas-liquid contact apparatus such as packed column, a bubble column, a spray column, or a multi-staged column, may be employed. The alcohol to be used, is selected from alcohol components which may constitute said ester of nitrous acid.

The non-condensed gas to be contacted with the alcohol and the gas containing molecular oxygen, may be introduced into the regeneration column individually or in a mixed state.

In the regeneration column, a part of nitrogen monoxide is oxidized to nitrogen dioxide and at the same time, these substances are allowed to be absorbed and react with an alcohol and thereby to be regenerated as an ester of nitrous acid.

In this step, it is preferred to control the concentration of nitrogen monoxide in the gas withdrawn from the regeneration column to be within a range of from 2 to 7% by volume, and to maintain the gas to contain as little nitrogen as possible, most preferably with substantially no nitrogen dioxide and oxygen. Namely, if the concentration of nitrogen monoxide in the regenerated gas is greater than the above mentioned upper limit, the reaction rate for the formation of the diester of oxalic acid is decreased and the yield is lowered, when said gas is recycled for use in the reactor of the first step. On the other hand, if said concentration is lower than the above-mentioned lower limit, the amounts of nitrogen dioxide and oxygen in the regenerated gas will be increased, and they will be a factor for substantial degradation of the activity of the platinum group metal catalyst of the first step.

Accordingly, it is preferred that from 0.08 to 0.2 mole, in terms of oxygen, of the gas containing molecular oxygen, relative to one mole of nitrogen monoxide in the gas introduced to the regeneration column, is supplied and these gases are contacted with the alcohol at a temperature of at most the boiling point of the alcohol thus used. The contact time is preferably from 0.5 to 20 seconds. Further, the alcohol is used in such an amount as to be sufficient for completely absorbing and reacting the resulting nitrogen dioxide and an almost equimolar amount of nitrogen monoxide, and usually, from 2 to 5 parts by volume of the alcohol is preferably used relative to one part by volume of nitrogen monoxide in the gas introduced into the regeneration column.

Further, since this invention is a continuous process, a loss of a nitrogen component is unavoidable, and its supplementation may be made by supplying the ester of nitrous acid to the reactor of the first step, or by introducing a nitrogen oxide such as nitrogen monoxide, nitrogen dioxide, dinitrogen trioxide or dinitrogen tetroxide, or nitric acid into the regeneration column of the third step.

Further, in case the content of nitrogen monoxide in the non-condensed gas in the second step is great, and if the ester of nitrous acid is obtainable in an excess amount during the regeneration of the nitrogen monoxide into the ester of nitrous acid in the third step, the entire amount of the non-condensed gas needs not be led to the regeneration column and a part thereof may directly be recycled to the reactor of the first step.

The gas containing the ester of nitrous acid and withdrawn from the regeneration column, is recycled to the reactor of the first step. Further, this regenerated gas may be mixed with another starting material i.e. carbon monoxide, and then the mixture may be supplied to the reactor.

When the regenerated ester of nitrous acid is an ester of an alcohol having at least 4 carbon atoms, such as n-butyl nitrite, or n-amyl nitrite, it forms an azeotropic mixture with water formed as a by-product by the regeneration reaction and consequently, water is contained in the regenerated gas. Accordingly, if this gas is supplied in that state to the reactor of the first step, the water hinders the reaction for the formation of the diester of oxalic acid. Therefore, it is desirable that water in the gas is removed by an operation such as distillation before the gas is recycled to the reactor. On the other hand, when the regenerated ester of nitrous acid is methyl nitrite, ethyl nitrite, n-propyl nitrite, or i-propyl nitrite, it does not form an azeotropic mixture with water formed as a by-product by the regeneration reaction, and accordingly, the regenerated gas contains no water and may therefore be recycled to the reactor as it is.

The liquid withdrawn from the regeneration tower is an alcohol solution containing water formed as by-product by the regeneration reaction. This may be refined by an operation such as distillation to such an extent that the water content in the alcohol becomes to be at most 5% by volume, preferably at most 2% by volume, and may then be reused as an alcohol source for the third step, and in a proper case, as an alcohol source for the second step.

FOURTH STEP

The condensed liquid separated in the second step is led to a distillation column and distilled by a usual operation, whereby the intended product of the diester of oxalic acid is obtained as the distillation residue.

In the distillate, there are contained, in addition to the alcohol, a diester of carbonic acid formed as a by-product by the catalytic reaction in the first step, and a small amount of an ester of formic acid.

FIFTH STEP

The distillate of the fourth step is led to a hydrolysis column and contacted with steam, whereby the diester is carbonic acid in the distillate is hydrolized to the alcohol and carbon dioxide.

This hydrolysis can readily be carried out by a gas phase reaction in the presence of an alumina catalyst such as, e.g., Neobead P (trade name) made by Mizusawa Kagaku Co., at a temperature of from 150° to 250° C. Further, in this step, the ester of formic acid present, in a small amount, in the distillate, will likewise be hydrolized and converted to an alcohol.

The gaseous alcohol withdrawn from the hydrolysis column is condensed and then recycled as a part of the alcohol source for the regeneration column of the third step. Further, in the case where in the second step, the condensation is carried out while contacting the non-condensed gas with an alcohol, a part of the alcohol obtained in the fifth step may be supplied as the alcohol source.

Further, the distillation column and the hydrolysis column used in the fourth and fifth steps, may be usual apparatus such as a packed column, a multi-stage column, a forced agitation type thin film column.

Now, the process of the present invention will be described in detail in accordance with the flow sheet diagram (FIG. 1) illustrating an embodiment of the invention. In the drawing, 1 designates a reactor, 2 designates a condenser, 3 designates a regeneration column 4 designates a distillation column, 5 designates a hydrolysis column, 6 designates a heat exchanger, and 11 to 29 represent conduits (pipe lines).

A gas containing carbon monoxide, an ester of nitrous acid, nitrogen monoxide and so on is compressed by a gas-recycling device (not shown) and introduced into the top of a multitubular reactor 1 having reaction tubes packed with a platinum group metal catalyst, via a conduit 21. A catalytic reaction is carried out in the gaseous phase in the reactor 1. The gas formed by the reaction upon passing through the catalyst layer, is withdrawn from the bottom and introduced to a condenser 2 via a conduit 11.

In the condenser 2, while being contacted with an alcohol supplied from a conduit 13, the reaction-formed gas is condensed, and the condensed liquid containing mainly the diester of oxalic acid is led from the bottom via a conduit 14 to a distillation column 4. On the other hand, a non-condensed gas containing non-reacted carbon monoxide and the ester of nitrous acid, nitrogen monoxide formed as a by-product and so on, is introduced from the top of the bottom of the regneration column 3 via a conduit 12.

In the regeneration column 3, the non-condensed gas is countercurrently contacted and reacted with a gas containing molecular oxygen and supplied to the bottom via a conduit 16 and an alcohol supplied to the top via a conduit 18, whereupon an ester of nitrous acid is formed.

In the regeneration column 3, the oxidation reaction of nitrogen monoxide to nitrogen dioxide is followed by the absorption reaction thereof to the alcohol. If the nitrogen source for the formation of the ester of nitrous acid is inadequate, a nitrogen oxide may be supplied via conduit 15. The gas containing the ester of nitrous acid formed in the regeneration column 3 is recycled to the reactor 1 via conduits 19 and 21 together with carbon monoxide supplied anew from a conduit 20. On the other hand, the water formed as a by-product in the regeneration column 3 is withdrawn in a form of an aqueous alcohol solution from the bottom via a conduit 17. This aqueous alcohol solution is subjected to an operation such as distillation to remove the water in the liquid, and thereafter may be reused as an alcohol source to be supplied to the regeneration column 3 or the condenser 2 via said conduit 18 or 13.

In the distillation column 4, the alcohol and diester of carbonic acid as a by-product are distilled and the intended product of the diester of oxalic acid in a form of a liquid is withdrawn via a conduit 22.

The distillate is passed through a conduit 23, heated by a heat exchanger 6, passed through a conduit 24, mixed with steam supplied from a conduit 25 and led to a hydrolysis column 5.

In the hydrolysis column 5, the diester of carbonic acid and the ester of formic acid in the gas, will be hydrolyzed in the gaseous phase into the alcohol and carbon dioxide by the action of an alumina catalyst. The formed gaseous alcohol is passed through a conduit 26, cooled by a heat exchanger 6, and then freed from the carbon dioxide in the gas and at the same time condensed, in a condenser (not shown). Then, the liquid alcohol is passed through conduits 27, 28, and recycled as an alcohol source to be supplied to the regeneration column 3 via a conduit 18.

Further, a part of this alcohol may also be reused as an alcohol source to be supplied to the condenser 2 via conduits 29 and 13, as the case requires.

Now, the invention will be described in detail with reference to the following Examples.

EXAMPLE 1

In the tubes of a stainless multi-tubular reactor, which has 6 tubes having an inside diameter of 36.7 mm and a height of 550 mm, there was packed 3 kg (3 liters) of a $\gamma$-alumina catalyst in a form of pellets having a diameter of 5 mm and a height of 3 mm and carrying 0.5% by weight of palladium.

A gaseous mixture of carbon monoxide and the regenerated gas from the regeneration column mentioned below [pressure: 0.2 kg/cm$^2$ (gauge pressure), composition: 22.0% by volume of carbon monoxide, 9.1% by volume of methyl nitrite, 3.1% by volume of nitrogen monoxide, 9.4% by volume of methanol, 8.5% by volume of carbon dioxide and 47.0% by volume of nitrogen] was preheated to about 90° C. by a heat exchanger, and then introduced from the top of this catalyst layer at a rate of 12.0 Nm$^3$/hr. by a diaphragm gas-recycling pump, and the temperature of the catalyst layer was maintained at 104° to 117° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and from the top of the condenser, methanol was introduced at a rate of 5.6 liters/hr., whereby the countercurrent contact was carried out at a temperature of about 35° C. (i.e. 30° C. at the top of the condenser and 40° C. at the bottom of the condenser). From the bottom of the condenser, there was obtained 2.8 kg/hr. of a condensed liquid (composition: 46.6% by weight of dimethyl oxalate, 4.9% by weight of dimethyl carbonate, 0.03% by weight of methyl formate and 48.0% by weight of methanol). On the other hand, from the top of the condenser 13.6 Nm$^3$/hr. of a non-condensed gas (composition: 15.4% by volume of carbon monoxide, 3.9% by volume of methyl nitrite, 6.8% by volume of nitrogen monoxide, 24.2% by volume of methanol, 7.6% by volume of carbon dioxide and 41.4% by volume of nitrogen) was obtained.

To this non-condensed gas, 140 liters/hr. of oxygen and 9 liters/hr. of nitrogen monoxide were mixed (the molar ratio of oxygen to nitrogen monoxide in the gas being 0.15) and the mixture was led to the bottom of the gas-liquid contact type regeneration column having an inner diameter of 158 mm and a height of 1,400 mm. From the top of the column, methanol (including the methanol recycled from the regeneration column), was supplied at a rate of 40 liters/hr. (1.77 liters/hr. of which was the one supplied from the hydrolysis column mentioned below). The countercurrent contact was carried out at a temperature of about 35° C. (i.e. 30° C. at the top of the column and 40° C. at the bottom of the column), whereby nitrogen monoxide in the gas was regenerated into methyl nitrite. To 14.2 Nm$^3$/hr. of the regenerated gas from the regeneration column (composition: 15.4% by volume of carbon monoxide, 8.0% by volume of methyl nitrite, 2.8% by volume of nitrogen monoxide, 24.2% by volume of methanol, 7.6% by volume of carbon dioxide and 41.3% by volume of nitrogen), there was added 550 liters/hr. of carbon monoxide, and the mixture was supplied to and compressed by said gas recycling pump. The discharged gas was cooled to 20° C. to remove condensed methanol, and then led to the reactor.

On the other hand, 1.2 liters/hr. of an aqueous methanol solution containing 20.0% by weight of water, withdrawn from the regeneration column, was subjected to distillation to remove water and then reused as a methanol source of said column. To a distillation column having an inside diameter of 30 mm and a height of 3,000 mm, 2.8 kg/hr. of the condensed liquid withdrawn from said condenser was introduced and distilled at a temperature of 63° C. at the top and 166° C. at the bottom. From the bottom, 1.32 kg/hr. of a dimethyl oxalate liquid having a purity of 98.0% by weight was obtained. On the other hand, 0.96 Nm$^3$/hr. of a gaseous distillate composed of 96.7% by volume of methanol, 3.2% by volume of dimethyl carbonate and 0.02% by volume of methyl formate, was obtained.

This gaseous distillate was led to a hydrolysis column having an inside diameter of 28.4 mm and a height of 1,000 mm [packed with 500 ml of Neobead P (trade name) made by Mizusawa Kagaku Co.] and contacted with 50 g/hr. of steam at about 200° C., whereby dimethyl carbonate and methyl formate in the gas were hydrolized. The methanol thereby obtained was recycled as a methanol source for said regeneration column at a rate of 1.77 liters/hr.

The initial space time yield of dimethyl oxalate in this Example was 432 g/l.hr. and no decrease in the space time yield was observed even after 480 hours of this continuous reaction.

EXAMPLE 2

In the tubes of a stainless multi-tubular reactor, which has 6 tubes having an inside diameter of 36.7 mm and a height of 550 mm, there was packed 2.5 kg (2.5 liters) of a γ-alumina catalyst in a form of pellets having a diameter of 5 mm and a height of 3 mm and carrying 0.5% by weight of palladium.

A gaseous starting material compressed to a pressure of 1.8 kg/cm$^2$ (gauge pressure) (composition: 20.0% by volume of carbon monoxide, 15.1% by volume of methyl nitrite, 3.1% by volume of nitrogen monoxide, 13.2% by volume of methanol, 2.0% by volume of carbon dioxide and 46.9% by volume of nitrogen) was preheated to about 90° C. by a heat exchanger, and then introduced from the top of this catalyst layer at a rate of 5.4 Nm$^3$/hr. by a diaphragm gas-recycling pump, and the temperature of the central portion of the catalyst layer was maintained at about 110° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and from the top of the condenser, methanol was introduced at a rate of 1.3 liters/hr., whereby the countercurrent contact was carried out at a temperature of 40° C. at the top of the condenser and 43° C. at the bottom of the condenser. From the bottom of the condenser, there was obtained 2.2 kg/hr. of a condensed liquid (composition: 48.0% by weight of dimethyl oxalate, 1.5% by weight of dimethyl carbonate, 0.3% by weight of methyl formate and 48.0% by weight of methanol). On the other hand, from the top of the condenser, 5.0 Nm$^3$/hr. of a non-condensed gas (composition: 13.3% by volume of carbon monoxide, 7.4% by volume of methyl nitrite, 11.9% by volume of nitrogen monoxide, 14.2% by volume of methanol, 2.4% by volume of carbon dioxide and 50.9% by volume of nitrogen) was obtained.

To this non-condensed gas, 119.0 liters/hr. of oxygen was mixed (the molar ratio of oxygen to nitrogen monoxide in the gas being 0.2) and the mixture was led to the bottom of the gas-liquid contact type regeneration column having an inner diameter of 158 mm and a height of 1,400 mm. From the top of the column, methanol was supplied at a rate of 5.0 liters/hr. (1.33 liters/hr. of which was the one supplied from the hydrolysis column mentioned below). The countercurrent contact was carried out at a temperature of 40° C. at the top of the column and 42° C. at the bottom of the column, whereby nitrogen monoxide in the gas was regenerated into methyl nitrite. The regenerated gas from the regeneration column (composition: 13.0% by volume of carbon monoxide, 16.3% by volume of methyl nitrite, 3.4% by volume of nitrogen monoxide, 14.7% by volume of methanol, 2.3% by volume of carbon dioxide and 50.0% by volume of nitrogen), was supplied to and compressed by said gas recycling pump at a rate of 5.1 Nm$^3$/hr. To 4.7 Nm$^3$/hr. of the discharged gas, there was added 0.7 Nm$^3$/hr. of a gaseous mixture containing 66.8% by volume of carbon monoxide, 6.3% by volume of methyl nitrite, 1.3% by volume of methanol and 25.6% by volume of nitrogen, and the mixture was led to the reactor.

On the other hand, 4.2 liters/hr. of a methanol solution containing 5.0% by weight of water, withdrawn from the regeneration column, was subjected to distillation to remove water and then reused as a methanol source for said column.

To a distillation column having an inside diameter of 30 mm and a height of 3,000 mm, 2.2 kg/hr. of the condensed liquid withdrawn from said condenser was introduced, and distilled at a temperature of 63° C. at the top and 166° C. at the bottom. From the bottom, 1.07 kg/hr. of a dimethyl oxalate liquid having a purity of 99.0% by weight was obtained. On the other hand, 0.74 $Nm^3$/hr. of a gaseous distillate composed of 98.50% by volume of methanol, 1.13% by volume of dimethyl carbonate and 0.29% by volume of methyl formate, was obtained.

This gaseous distillate was led to a hydrolysis column having an inside diameter of 28.4 mm and a height of 1,000 mm [packed with 500 ml of Neobead P (trade name) made by Mizusawa Kagaku Co.] and contacted with 17.0 g/hr. of steam at about 200° C., whereby dimethyl carbonate and methyl formate in the gas were hydrolized. The methanol thereby obtained was recycled as a methanol source for said regeneration column at a rate of 1.33 liters/hr.

The initial space time yield of dimethyl oxalate in this Example was 421 g/l.hr. and no decrease in the space time yield was observed even after 480 hours of this continuous reaction.

EXAMPLE 3

In the tubes of a stainless multi-tubular reactor, which has 8 tubes having an inside diameter of 28.0 mm and a height of 1,000 mm, there was packed 3.85 kg (3.85 liters) of a γ-alumina catalyst in a form of pellets having a diameter of 5 mm and a height of 3 mm and carrying 0.5% by weight of palladium.

A gaseous starting material compressed under a pressure of 1.8 kg/$cm^2$ (gauge pressure) (composition: 20.0% by volume of carbon monoxide, 7.0% by volume of ethyl nitrite, 3.0% by volume of nitrogen monoxide, 6.0% by volume of ethanol, 3.2% by volume of carbon dioxide and 59.8% by volume of nitrogen) was preheated to about 90° C. by a heat exchanger and then introduced from the top of the catalyst layer by a diaphragm gas recycling pump at a rate of 23.0 $Nm^3$/hr., and the temperature of the central portion of the catalyst layer was maintained to be about 110° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and from the top of the condenser, ethanol was introduced at a rate of 8.0 liters/hr., whereby the countercurrent contact was carried out at a temperature of 60° C. at the top and 63° C. at the bottom. From the bottom of the condenser, there was obtained 2.5 kg/hr. of a condensed liquid (composition: 54.7% by weight of diethyl oxalate, 1.8% by weight of diethyl carbonate, 0.3% by weight of ethyl formate and 41.6% by weight of ethanol). On the other hand, from the top of the condenser, 24.9 $Nm^3$/hr. of a non-condensed gas (composition: 16.7% by volume of carbon monoxide, 4.6% by volume of ethyl nitrite, 4.6% by volume of nitrogen monoxide, 16.0% by volume of ethanol, 3.0% by volume of carbon dioxide and 54.0% by volume of nitrogen) was obtained.

To this non-condensed gas, 118.5 Nl/hr. of oxygen was mixed (the molar ratio of oxygen to nitrogen monoxide in the gaseous mixture being 0.104) and the mixture was led to the bottom of the gas-liquid contact type regeneration column having an inner diameter of 158 mm and a height of 1,400 mm. From the top of the column, ethanol is supplied at a rate of 2.3 liters/hr. (1.33 liters/hr. of which was supplied from the hydrolysis column mentioned below). The countercurrent contact was carried out at a temperature of 40° C. at the top of the column and 42° C. at the bottom of the column, whereby nitrogen monoxide in the gas was regenerated into ethyl nitrite. The regenerated gas from the regeneration column (composition: 18.4% by volume of carbon monoxide, 7.1% by volume of ethyl nitrite, 3.1% by volume of nitrogen monoxide, 6.2% by volume of ethanol, 3.3% by volume of carbon dioxide and 60.9% by volume of nitrogen), was supplied to and compressed by said gas recycling pump at a rate of 22.6 $Nm^3$/hr. To 22.3 $Nm^3$/hr. of the discharged gas, there was added 0.7 $Nm^3$/hr. of a gaseous mixture containing 71.5% by volume of carbon monoxide, 4.4% by volume of ethyl nitrite, 0.6% by volume of ethanol, and 23.6% by volume of nitrogen, and the mixture was led to the reactor.

On the other hand, 8.9 liters/hr. of an ethanol solution containing 4.3% by weight of water, withdrawn from the regeneration column, was subjected to dehydration and then reused as an ethanol source for said column.

To a distillation column having an inside diameter of 30 mm and a height of 3,000 mm, 2.5 kg/hr. of the condensed liquid withdrawn from said condenser was introduced and distilled at a temperature of 78° C. at the top and 185° C. at the bottom. From the bottom, 1.38 kg/hr. of a diethyl oxalate liquid having a purity of 98.9% by weight was obtained. On the other hand, 0.52 $Nm^3$/hr. of a gaseous distillate composed of 97.8% by volume of ethanol, 1.7% by volume of diethyl carbonate and 0.5% by volume of ethyl formate, was obtained.

This gaseous distillate was led to a hydrolysis column having an inside diameter of 28.4 mm and a height of 1,000 mm [packed with 500 ml of Neobead P (trade name) made by Mizusawa Kagaku Co.] and contacted with 18.0 g/hr. of steam at about 200° C., whereby diethyl carbonate and ethyl formate in the gas were hydrolized. The ethanol thereby obtained was recycled as a ethanol source for said regeneration column at a rate of 1.33 liters/hr.

The initial space time yield of diethyl oxalate in this Example was 355 g/l.hr. and no decrease in the space time yield was observed even after 480 hours of this continuous reaction.

We claim:

1. A process for the continuous preparation of a diester of oxalic acid, which comprises
   (1) a first step of passing gas containing carbon monoxide and an ester of a saturated monohydric aliphatic or alicyclic alcohol having 1 to 8 carbon atoms with nitrous acid into a reactor packed with a solid catalyst comprising a platinum group metal or its salt, and catalytically reacting said carbon monoxide and ester of nitrous acid in the gaseous phase at a temperature of from 50° to 200° C. and a pressure of from ambient pressure to 10 kg/$cm^2$ (gauge) to obtain a product containing (i) a diester of oxalic acid together with (ii) a by-product diester of carbonic acid and (iii) also containing nitrogen monoxide;

(2) a second step of passing the product of the first step to a condenser to separate said product into a non-condensed gas containing nitrogen monoxide formed by the catalytic reaction of the first step from a condensed liquid containing (i) the diester of oxalic acid together with (ii) said by-product diester of carbonic acid;

(3) a third step of passing the non-condensed gas of the second step to a regeneration column and therein contacting it with a gas containing molecular oxygen and an alcohol to react with nitrogen monoxide in said non-condensed gas to regenerate said ester of nitrous acid as the regeneration gas and to provide a concentration of nitrogen monoxide in said regeneration gas withdrawn from the regeneration column of from 2 to 7% by volume, and recycling said regeneration gas containing said ester of nitrous acid to the reactor of the first step;

(4) a fourth step of passing the condensed liquid of the second step to a distillation column and distilling out an alcohol containing said diester of carbonic acid formed as a by-product by the catalytic reaction of the first step, and obtaining a liquid diester of oxalic acid; and (5) a fifth step of passing the distillate of the fourth step to a hydrolysis column and hydrolyzing the diester of carbonic acid in the gas into its acid and alcohol components and recycling the alcohol thereby obtained to the third step as an alcohol source for the third step.

2. The process as claimed in claim 1, wherein said solid catalyst comprises palladium or a palladium salt.

3. The process as claimed in claim 1 or 2, wherein said catalytic reaction is carried out at a temperature of from 80° to 150° C.

4. The process as claimed in claim 1, wherein the product of the first step is contacted with an alcohol in said condenser and is cooled in said condenser at a temperature of at most the boiling point of said alcohol.

5. The process as claimed in claim 4, wherein said alcohol is a lower alcohol having 1 to 4 carbon atoms.

6. The process as claimed in claim 1, wherein the amount of said gas containing molecular oxygen in the third step is in the range of from 0.08 to 0.2 mole in terms of oxygen relative to one mole of nitrogen monoxide passed into in said regeneration column.

7. The process as claimed in claim 1, wherein the amount of the alcohol used in the third step is from 2 to 5 parts by volume relative to one part by volume of nitrogen monoxide passed into said regeneration column.

8. The process as claimed in claim 1, wherein the hydrolysis of the fifth step is carried out by a gas phase reaction in the presence of an alumina catalyst at a temperature of from 150° to 250° C.

9. The process as claimed in any one of claims 4, 6, 7 or 8, wherein said solid catalyst comprises palladium or a palladium salt, said catalytic reaction is carried out at a temperature of from 50° to 200° C. and under a pressure of between ambient pressure and 10 kg/cm$^2$ (gauge).

10. The process as claimed in any one of claims 2, 4 or 8, wherein the amount of the alcohol used in the third step is from 2 to 5 parts by volume relative to one part by volume of nitrogen monoxide passed into said regeneration column, and the amount of the alcohol used in the third step is from 2 to 5 parts by volume relative to one part by volume of nitrogen monoxide passed into said regeneration column.

11. The process as claimed in any one of claims 2, 6, 7 or 8, wherein said catalytic reaction is carried out at a temperature of from 80° to 150° C. and under a pressure of ambient pressure to 10 kg/cm$^2$ (gauge); the product of the first step is contacted with an alcohol in said condenser and is cooled in said condenser at a temperature of at most the boiling point of said alcohol; and said alcohol is a lower alcohol having 1 to 4 carbon atoms.

12. The process as claimed in claim 10, wherein said catalytic reaction is carried out at a temperature of from 80° to 150° C. and under a pressure of ambient pressure to 10 kg/cm$^2$ (gauge); the product of the first step is contacted with an alcohol in said condenser and is cooled in said condenser at a temperature of at most the boiling point of said alcohol; and said alcohol is a lower alcohol having 1 to 4 carbon atoms.

13. The process as claimed in any one of claims 1, 2, 4, 5, 6, 7 or 8, wherein said ester of nitrous acid is the methyl ester of nitrous acid, said diester of oxalic acid is the dimethyl oxalate, said diester of carbonic acid is the dimethyl ester of carbonic acid, and said alcohol is methyl alcohol.

14. The process as claimed in claim 11, wherein said ester of nitrous acid is the methyl ester of nitrous acid, said diester of oxalic acid is the dimethyl oxalate, said diester of carbonic acid is the dimethyl ester of carbonic acid, and said alcohol is methyl alcohol.

15. The process as claimed in claim 12, wherein said ester of nitrous acid is the methyl ester of nitrous acid, said diester of oxalic acid is the dimethyl oxalate, said diester of carbonic acid is the dimethyl ester of carbonic acid, and said alcohol is methyl alcohol.

16. The process as claimed in any one of claims 1, 2, 4, 5, 6, 7 or 8, wherein said ester of nitrous acid is the ethyl ester of nitrous acid, said diester of oxalic acid is the diethyl oxalate, said diester of carbonic acid is the diethyl ester of carbonic acid, and said alcohol is ethyl alcohol.

17. The process as claimed in claim 11, wherein said ester of nitrous acid is the ethyl ester of nitrous acid, said diester of oxalic acid is the diethyl oxalate, said diester of carbonic acid is the diethyl ester of carbonic acid, and said alcohol is ethyl alcohol.

18. The process as claimed in claim 12, wherein said ester of nitrous acid is the ethyl ester of nitrous acid, said diester of oxalic acid is the diethyl oxalate, said diester of carbonic acid is the diethyl ester of carbonic acid, and said alcohol is ethyl alcohol.

* * * * *